United States Patent
Thomassin et al.

(10) Patent No.: US 11,957,838 B2
(45) Date of Patent: Apr. 16, 2024

(54) PATIENT VENTILATOR, METHOD OF VENTILATING AN AIRWAY OF A PATIENT, AND ASSOCIATED COMPUTER PROGRAM PRODUCT

(71) Applicant: PRATT & WHITNEY CANADA CORP., Longueuil (CA)

(72) Inventors: Jean Thomassin, Sainte-Julie (CA); Jean-Gabriel Gauvreau, Varennes (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 933 days.

(21) Appl. No.: 16/939,501

(22) Filed: Jul. 27, 2020

(65) Prior Publication Data

US 2022/0023559 A1    Jan. 27, 2022

(51) Int. Cl.
*A61M 16/00*    (2006.01)
*A61M 16/20*    (2006.01)

(52) U.S. Cl.
CPC ...... *A61M 16/024* (2017.08); *A61M 16/0006* (2014.02); *A61M 16/0072* (2013.01); *A61M 16/202* (2014.02); *A61M 16/00* (2013.01); *A61M 2016/0027* (2013.01); *A61M 2205/3331* (2013.01); *A61M 2205/50* (2013.01)

(58) Field of Classification Search
CPC .............. A61M 16/00; A61M 16/0006; A61M 16/0057; A61M 16/0066; A61M 16/0072; A61M 16/024; A61M 16/202; A61M 16/203; A61M 16/204; A61M 16/205; A61M 2016/0027
See application file for complete search history.

(56) References Cited

U.S. PATENT DOCUMENTS

| | | | |
|---|---|---|---|
| 4,821,709 A | 4/1989 | Jensen | |
| 5,345,930 A | 9/1994 | Cardinal et al. | |
| 5,862,802 A * | 1/1999 | Bird | A61M 16/021 128/204.21 |
| 10,518,048 B2 | 12/2019 | Bobey et al. | |
| 2005/0051174 A1 | 3/2005 | Emerson | |
| 2008/0245368 A1 * | 10/2008 | Dunsmore | A61M 16/0006 128/205.24 |

(Continued)

FOREIGN PATENT DOCUMENTS

| | | |
|---|---|---|
| EP | 2854918 | 5/2018 |
| EP | 3313486 | 3/2020 |
| WO | 2011041838 | 4/2011 |

*Primary Examiner* — Joseph D. Boecker
(74) *Attorney, Agent, or Firm* — Norton Rose Fulbright Canada LLP

(57) ABSTRACT

There is described a ventilator for ventilating an airway of a patient. The ventilator is generally configured to perform a series of respiration cycles, wherein each respiration cycle includes the delivery of a main volume of fresh respiratory gas into the patient's airway, followed by the evacuation of a corresponding volume of used respiratory gas, and to further perform a series of subcycles during a corresponding one of the respiration cycles, wherein each subcycle includes the delivery of an auxiliary volume of fresh respiratory gas into the patient's airway, followed by the evacuation of a corresponding volume of used respiratory gas, the auxiliary volume being smaller than, and distinct from, the main volume.

20 Claims, 13 Drawing Sheets

(56) References Cited

U.S. PATENT DOCUMENTS

| | | | | |
|---|---|---|---|---|
| 2010/0180897 A1* | 7/2010 | Malgouyres | ...... | A61M 16/0009 128/204.23 |
| 2015/0165144 A1* | 6/2015 | Lee | ................... | A61M 16/0003 128/204.23 |
| 2017/0368410 A1* | 12/2017 | Brand | ................... | A61B 5/0823 |
| 2018/0361089 A1* | 12/2018 | Kim | ................... | A61M 16/0006 |
| 2021/0052844 A1* | 2/2021 | Oldfield | ................ | A61M 16/16 |

* cited by examiner

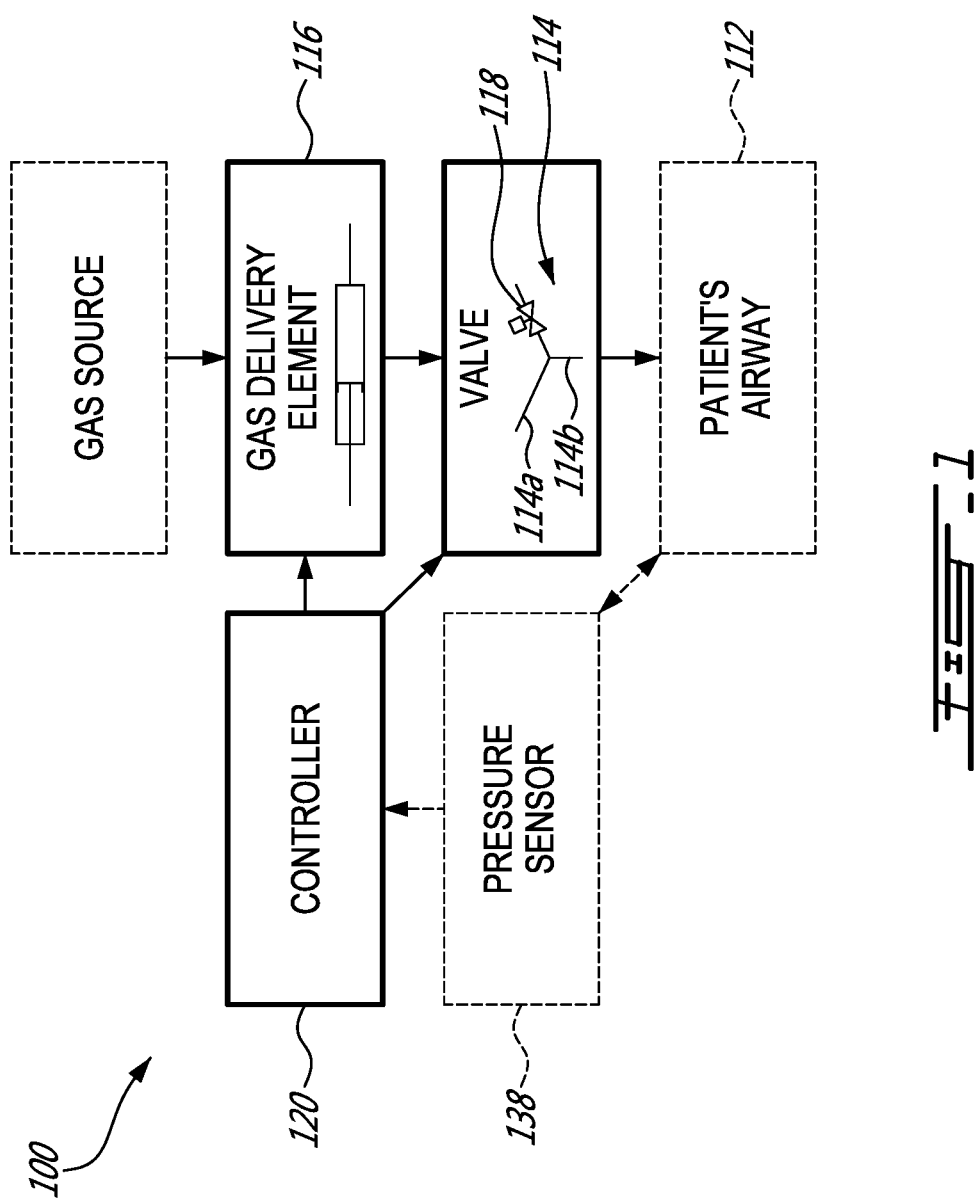

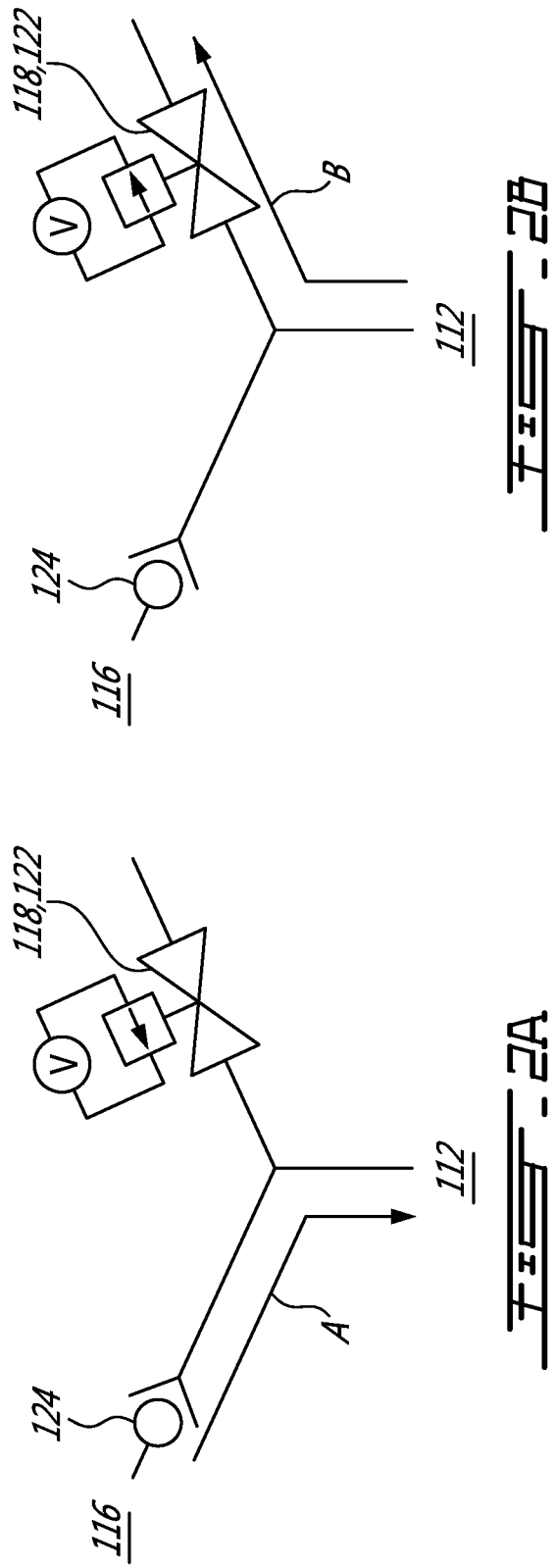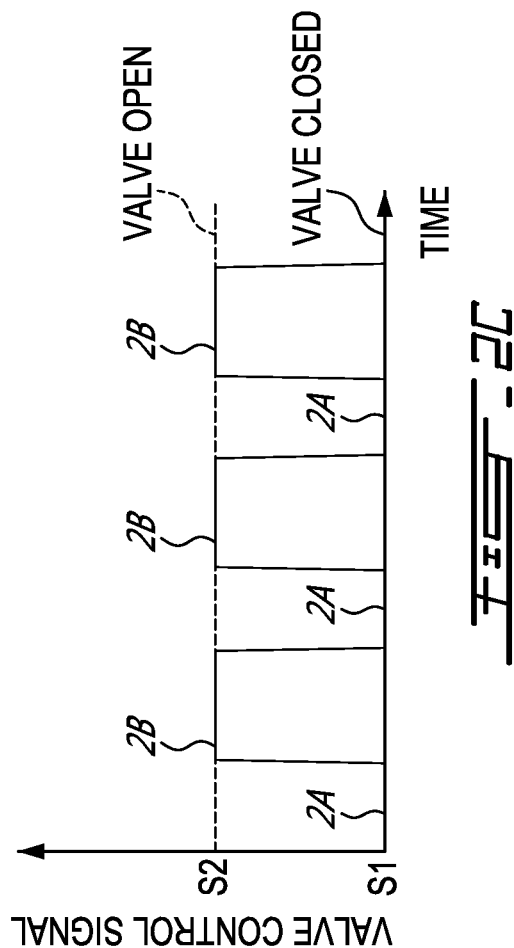

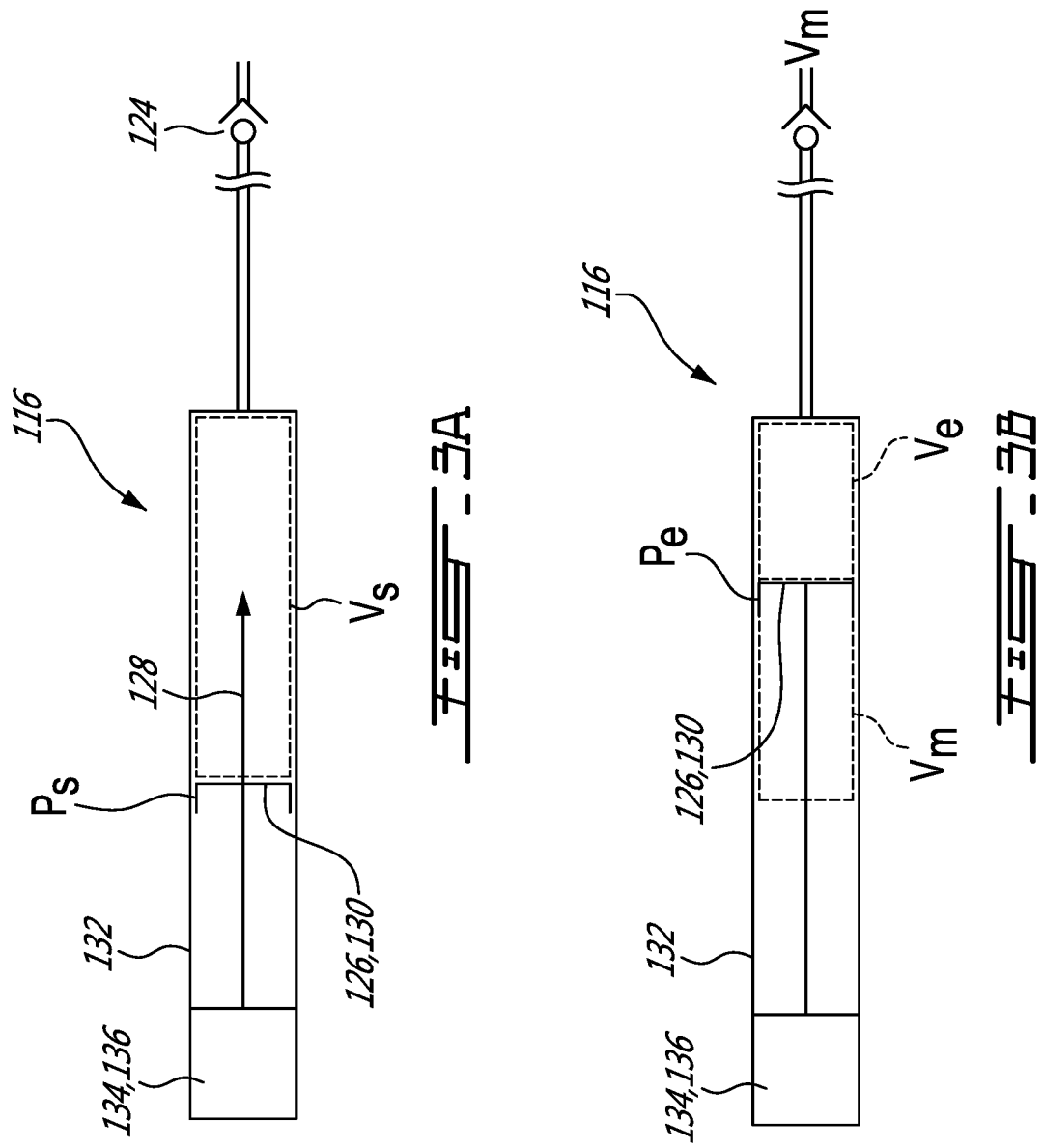

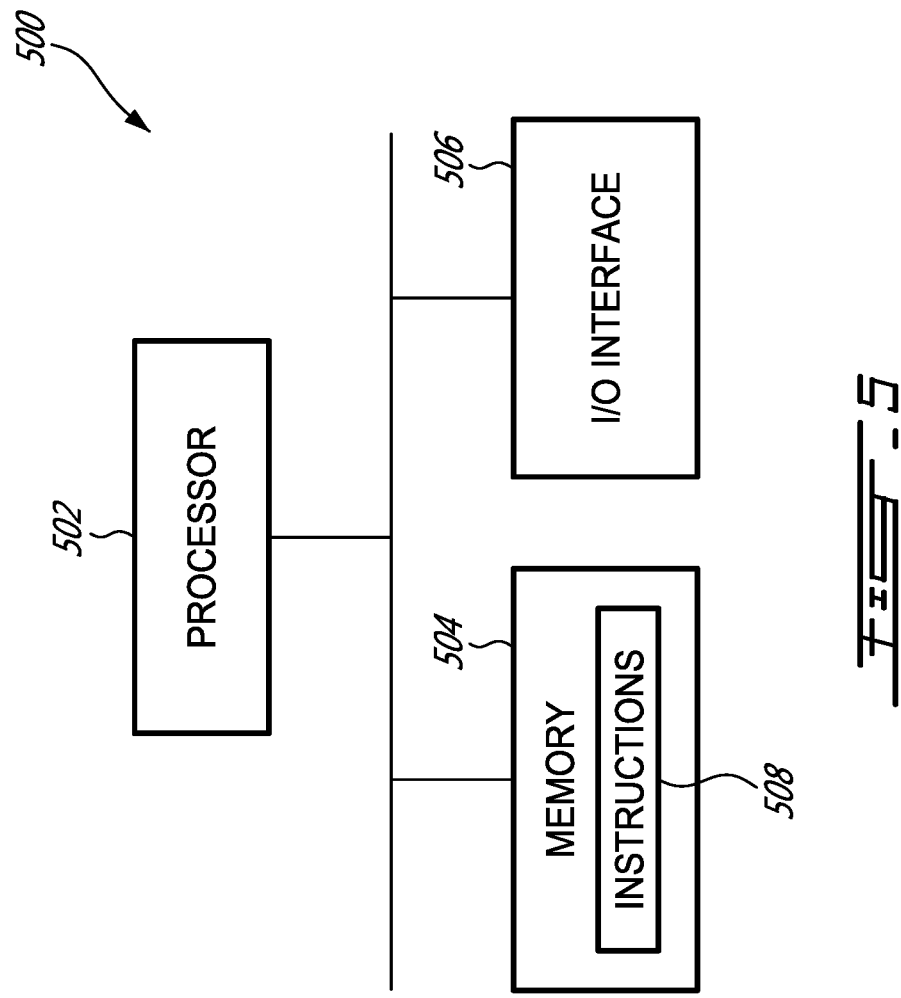

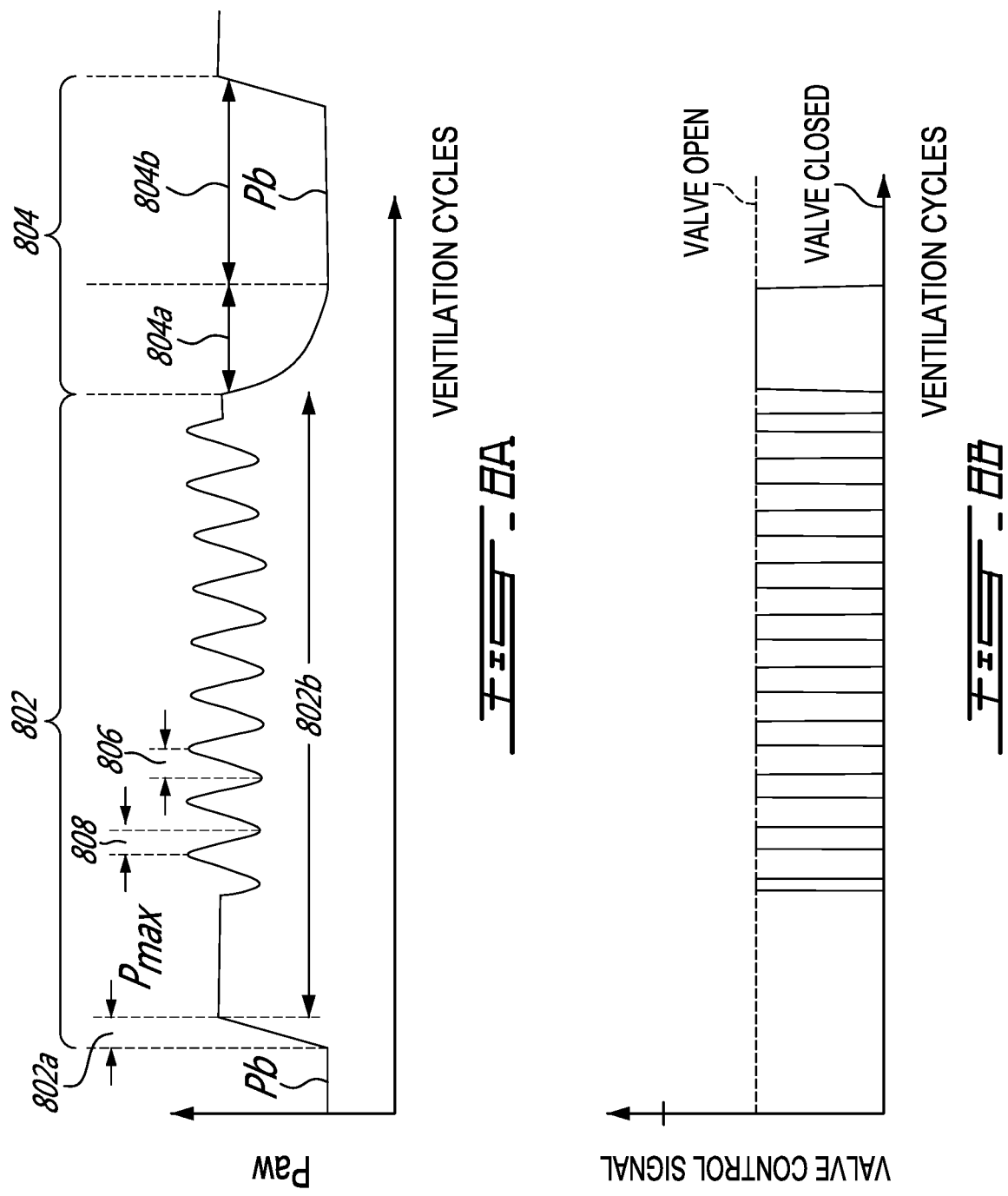

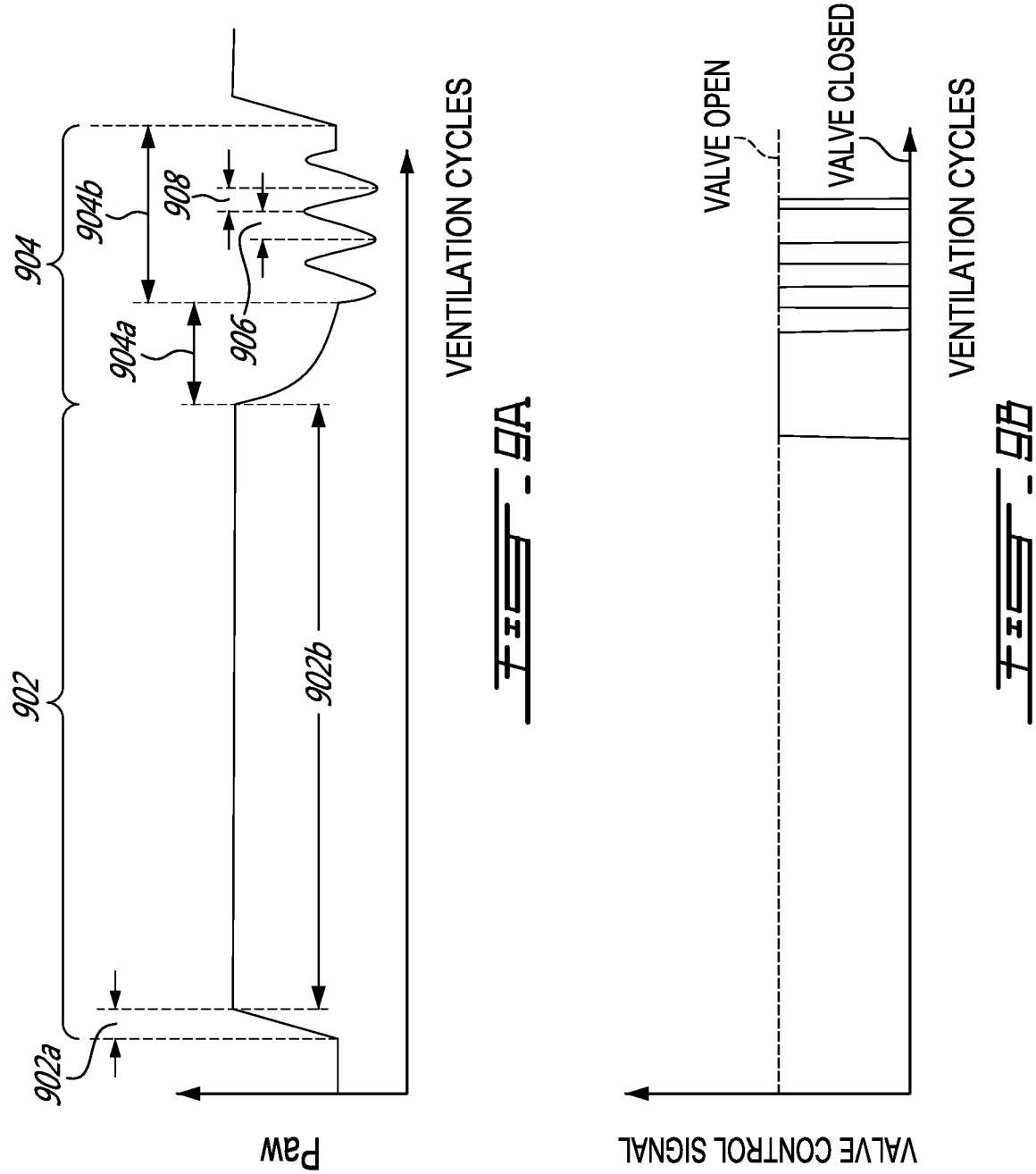

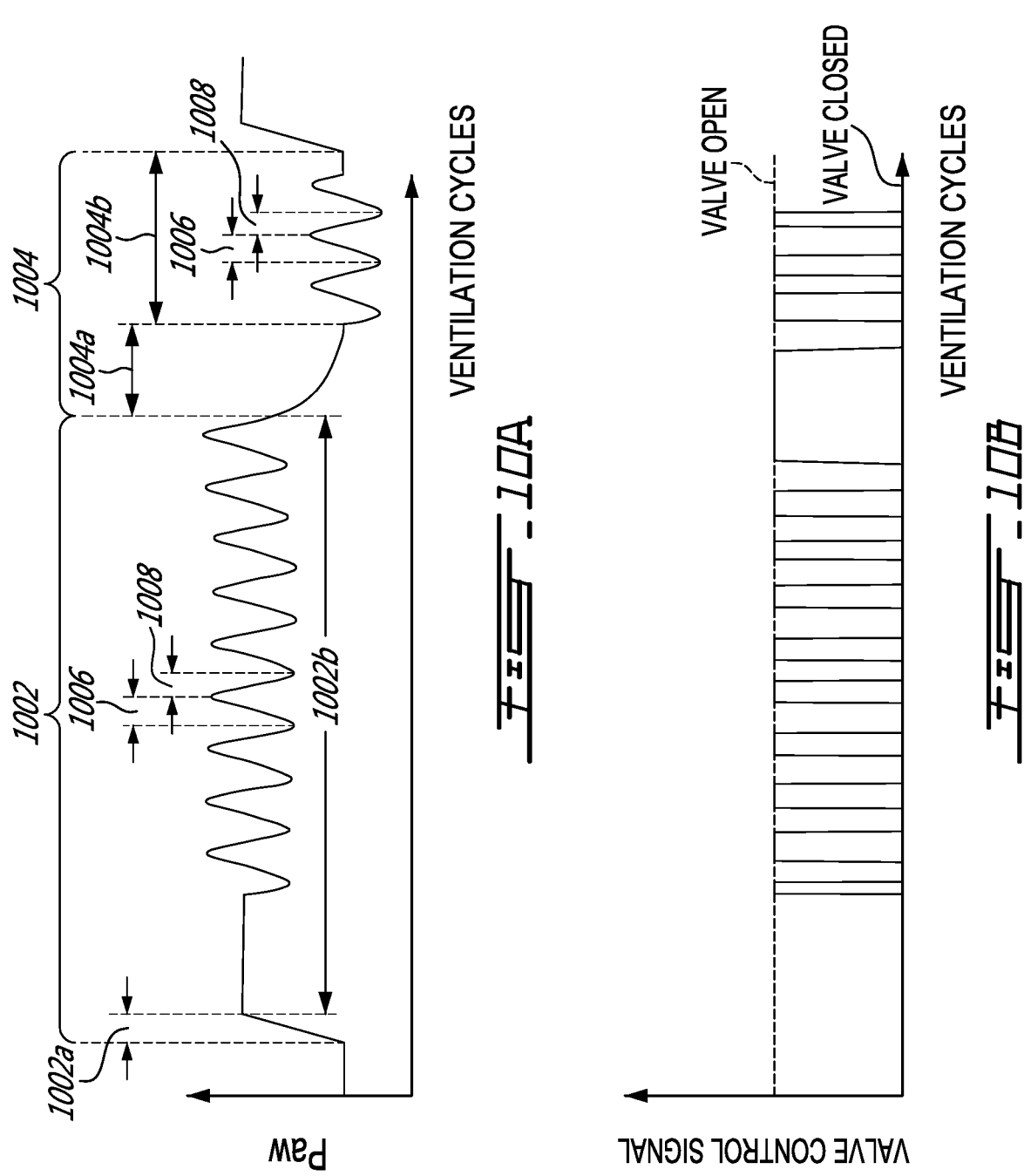

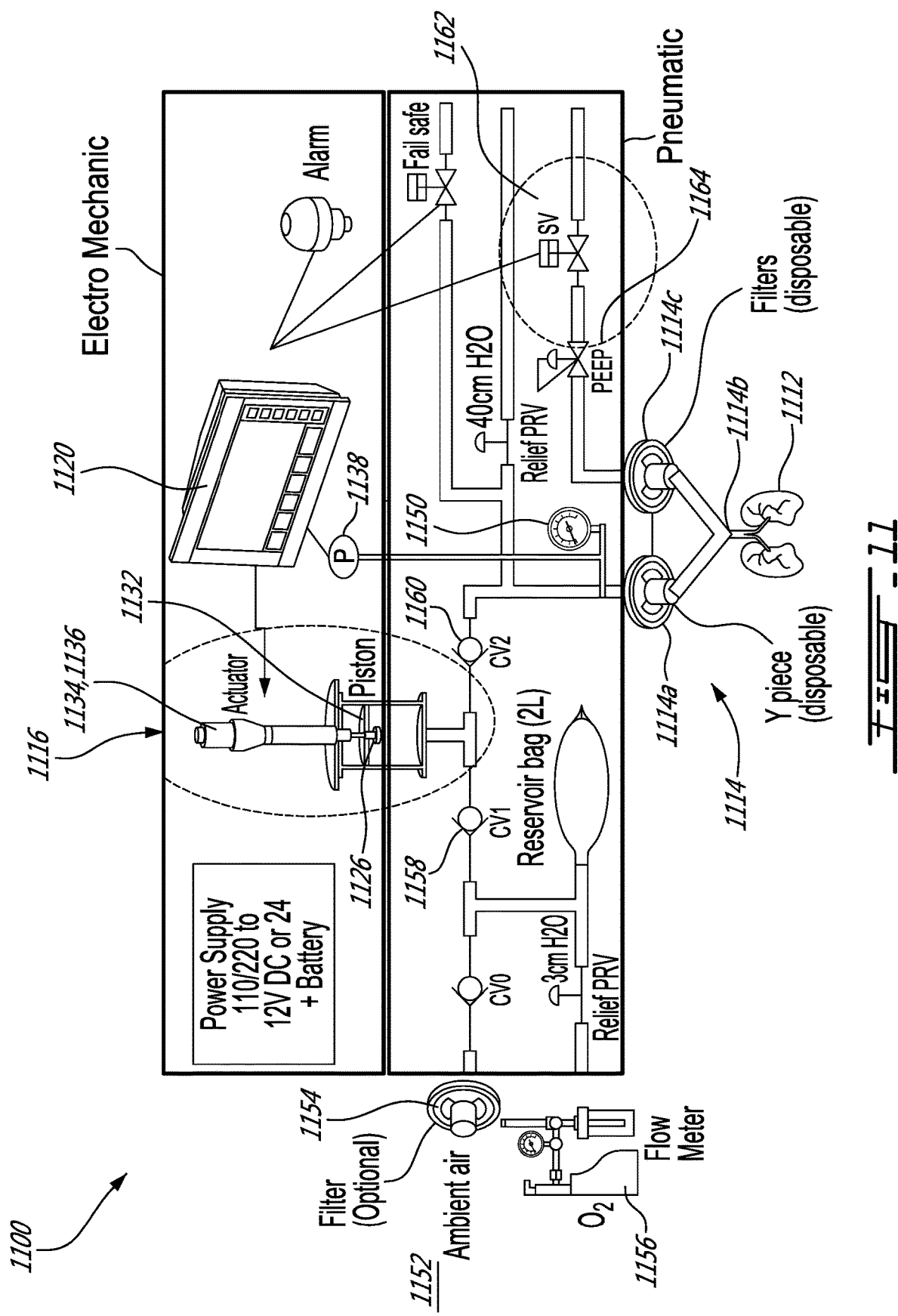

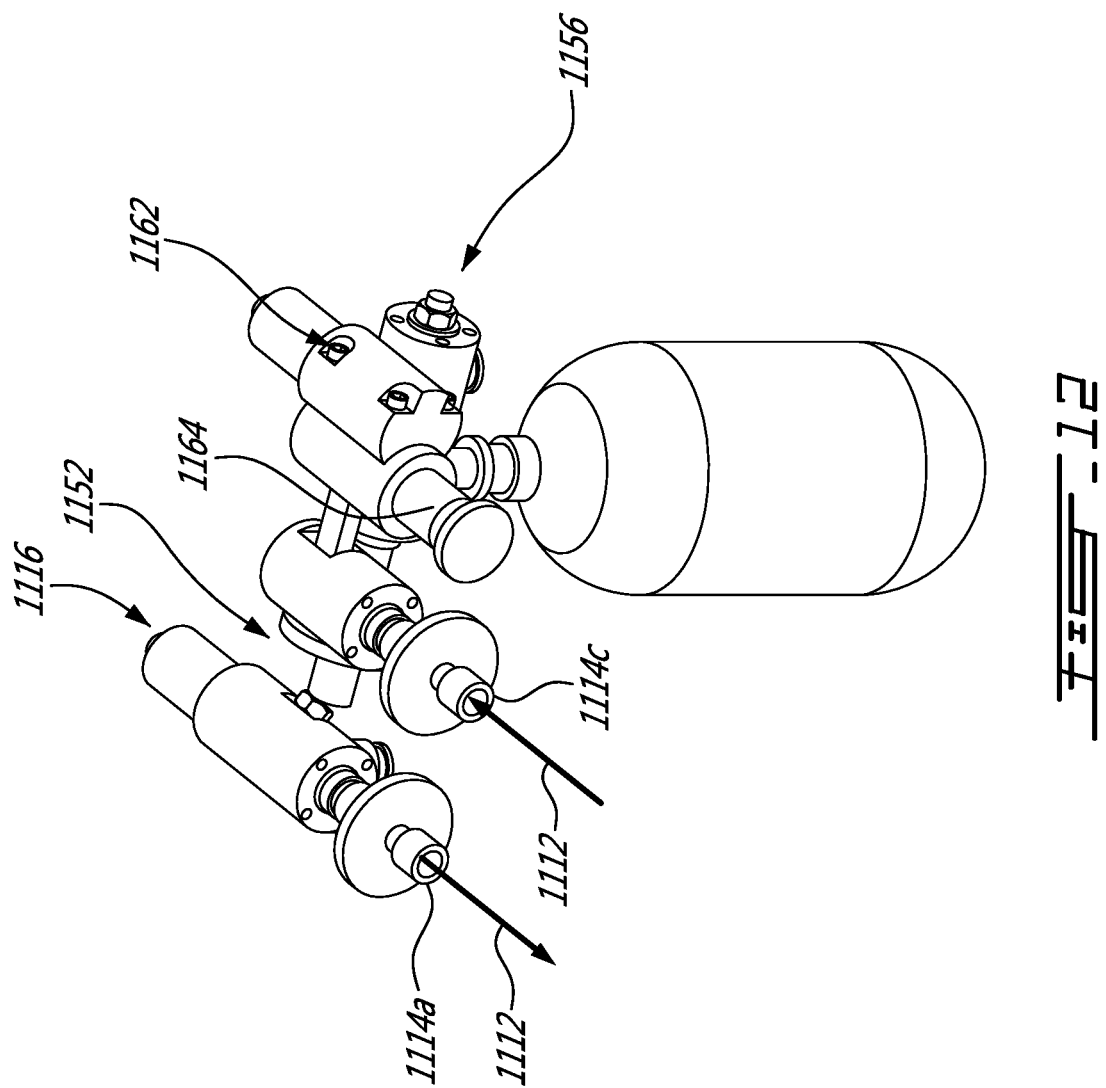

PATENT VENTILATOR, METHOD OF VENTILATING AN AIRWAY OF A PATIENT, AND ASSOCIATED COMPUTER PROGRAM PRODUCT

TECHNICAL FIELD

The application relates generally to ventilators, more particularly, to patient ventilators configured to ventilate patient airways.

BACKGROUND OF THE ART

Ventilators are machines used to deliver breaths to a patient who is physically unable to breathe, or who breathes insufficiently. More specifically, ventilators can be computerized/microprocessor-controlled machines configured to perform respiration cycles. Each respiration cycle includes the delivery of fresh air to the patient which recruits (i.e., opens) the lung tissues, and the evacuation of the used air thereafter. Patients suffering from some respiratory diseases, such as COVID-19, may experience stiffening of some of the lung tissues. This can lead to challenges in satisfactorily recruiting both softer lung tissues and stiffer lung tissues. Although existing ventilators are satisfactory to a certain degree, there remains room for improvement, especially in recruiting both softer lung tissues and stiffer lung tissues.

SUMMARY

In accordance with a first aspect of the present disclosure, there is provided a ventilator to ventilate an airway of a patient, the ventilator comprising: a conduit having an inlet in fluid communication with a patient port, said patient port being configured to be fluidly connected to said airway; a gas delivery element fluidly connected to said inlet and configured for selectively delivering fresh respiratory gas into the conduit; a valve fluidly connected to said conduit, said valve being selectively operable to vent the conduit and thereby evacuate used respiratory gas via the patient port; and a controller configured to alternatingly control the gas delivery element and the valve in a series of respiration cycles, wherein each respiration cycle includes the delivery of a main volume of fresh respiratory gas into the conduit, followed by the evacuation of a corresponding volume of used respiratory gas, said controller being further configured to alternatingly control the gas delivery element and the valve in a series of subcycles during a corresponding one of the respiration cycles, wherein each subcycle includes the delivery of an auxiliary volume of fresh respiratory gas into the conduit, followed by the evacuation of a corresponding volume of used respiratory gas, the auxiliary volume being smaller than, and distinct from, the main volume.

In accordance with a second aspect of the present disclosure, there is provided a method of ventilating an airway of a patient, said method comprising: ventilating said airway of said patient in accordance with a series of respiration cycles, each respiration cycle including the delivery of a main volume of fresh respiratory gas into said airway, followed by the evacuation of a corresponding volume of used respiratory gas; and during a corresponding one of said respiration cycles, ventilating said airway of said patient in accordance with a series of subcycles, wherein each subcycle includes the delivery of an auxiliary volume of fresh respiratory gas into the airway, followed by the evacuation of a corresponding volume of used respiratory gas, the auxiliary volume being smaller than, and distinct from, the main volume.

In accordance with a third aspect of the present disclosure, there is provided a computer program product stored in a non-transitory memory of a controller further having a processor, the computer program product having computer readable instructions which, when executed by the processor controls a patient ventilator, including the steps of: ventilating a conduit of said patient ventilator in accordance with a series of respiration cycles, each respiration cycle including the delivery of a main volume of fresh respiratory gas into said conduit, followed by the evacuation of a corresponding volume of used respiratory gas; and during a corresponding one of said respiration cycles, ventilating said cycle including the delivery of a main volume of fresh respiratory gas into said conduit of said patient in accordance with a series of subcycles, wherein each subcycle includes the delivery of an auxiliary volume of fresh respiratory gas into the cycle including the delivery of a main volume of fresh respiratory gas into said conduit, followed by the evacuation of a corresponding volume of used respiratory gas, the auxiliary volume of fresh respiratory gas being smaller than, and distinct from, the main volume of respiratory gas.

DESCRIPTION OF THE DRAWINGS

Reference is now made to the accompanying figures in which:

FIG. 1 is a schematic view of an example of a ventilator, shown with a conduit connected to a patient's airway, a valve, a gas delivery element and a controller, in accordance with one or more embodiments;

FIG. 2A is a schematic view of the valve of FIG. 1, shown with the valve at a closed position with fresh air flowing along a first flow direction towards the patient's airway, in accordance with one or more embodiments;

FIG. 2B is a schematic view of the valve of FIG. 1, shown with the valve at an open position with used air flowing along a second flow direction away from the patient's airway, in accordance with one or more embodiments;

FIG. 2C is a graph showing a valve control signal as a function of time, the valve control signal actuating the valve of FIG. 1 to move between the closed and open positions as shown in FIGS. 2A and 2B, in accordance with one or more embodiments;

FIG. 3A is a schematic sectional view of the gas delivery element of FIG. 1, shown with a moving element at a start position, in accordance with one or more embodiments;

FIG. 3B is a schematic sectional view of the gas delivery element of FIG. 1, shown with the moving element at an end position, in accordance with one or more embodiments;

FIG. 5 is a schematic view of an example of a computing device of the controller of FIG. 1, in accordance with one or more embodiments;

FIG. 8A is a graph of the airway pressure during an example respiration cycle, showing a series of respiratory cycles to which are superposed a series of subcycles during an inspiration phase of the respiratory cycle, in accordance with one or more embodiments;

FIG. 8B is a graph showing a valve control signal during the respiration cycle of FIG. 8A, in accordance with one or more embodiments;

FIG. 9A is a graph of the airway pressure during an example respiration cycle, showing a series of respiratory cycles to which are superposed a series of subcycles during an expiration phase of the respiratory cycle, in accordance with one or more embodiments;

FIG. 9B is a graph showing a valve control signal during the respiration cycle of FIG. 9A, in accordance with one or more embodiments;

FIG. 10A is a graph of the airway pressure during an example respiration cycle, showing a series of respiratory cycles to which are superposed a series of subcycles during both an inspiration phase and an expiration phase of the respiratory cycle, in accordance with one or more embodiments;

FIG. 10B is a graph showing a valve control signal during the respiration cycle of FIG. 10A, in accordance with one or more embodiments;

FIG. 11 is a schematic view of another example of a ventilator, in accordance with one or more embodiments;

FIG. 12 is an oblique view of a solenoid valve of the ventilator of FIG. 11, in accordance with one or more embodiments;

DETAILED DESCRIPTION

Figure 4A:
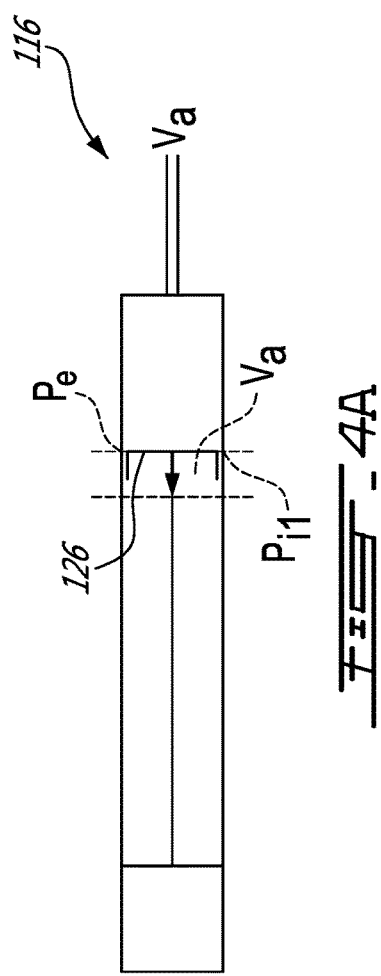
FIG. 4A is a schematic sectional view of the gas delivery element of FIG. 1, shown with the moving element at a first intermediate position, in accordance with one or more embodiments.

FIG. 1 shows an example of a ventilator 100 to ventilate an airway 112 of a patient, in accordance with an embodiment. As illustrated, the ventilator 100 has a conduit 114 with an inlet 114a in fluid communication with a patient port 114b. During use of the ventilator 100, the patient port 114b is configured to be connected to the airway 112 of the patient.

The ventilator 100 has a gas delivery element 116 which is fluidly connected to the inlet 114a and which is configured for selectively deliver fresh respiratory gas, for instance fresh air, into the conduit 114.

As shown, the ventilator 100 has a valve 118 which is fluidly connected to the conduit 114. The valve 118 is selectively operable to vent the conduit 114 and thereby evacuate used respiratory gas, e.g., used air, from the patient port 114b.

The ventilator 100 has a controller 120 configured to alternatingly control the gas delivery element 116 and the valve 118 in a series of respiration cycles. As such, the controller 120 may be communicatively coupled to the gas delivery element 116 and to the valve 118. Such a communicative coupling may be wired, wireless, or a combination of both depending on the embodiment. Each of these respiration cycles includes the delivery of a main volume Vm of fresh air into the conduit 114, followed by the evacuation of a corresponding volume Vm' of used air. The controller 120 is further configured to alternatingly control the gas delivery element 116 and the valve 118 in a series of subcycles during a corresponding one of the respiration cycles. Each of these subcycles includes the delivery of an auxiliary volume Va of fresh air into the conduit 114, followed by the evacuation of a corresponding volume Va' of used air. The subcycles are characterized in that the auxiliary volume Va is smaller than, and distinct from, the main volume Vm. In some embodiments, the subcycles are performed at an auxiliary respiratory rate Ra which is greater than a main respiratory rate Rm of the respiration cycles. For instance, the main respiratory rate Rm may range between 0.15 Hz and 0.50 Hz while the auxiliary respiratory rate Ra may range between 3 Hz and 50 Hz. In some embodiments, the auxiliary respiratory rate Ra may be ten times greater than the main respiratory rate Rm. The auxiliary volume Va may change from one subcycle to another. For instance, the auxiliary volume Va may correspond to a maximal tidal volume for the patient.

As such, it is intended that the gas delivery element 116 and the valve 118 are configured to ventilate the conduit 114, and therefore to the patient's airway 112, in accordance with the respiration cycles and associated subcycles. Hereinafter, the delivery of the main volume Vm of fresh air and the evacuation of the corresponding volume Vm' of used air are referred to as the main delivery and the main evacuation, respectively. Correspondingly, the delivery of the auxiliary volume Va of fresh air and the evacuation of the corresponding volume Va' of used air are referred to herein as the auxiliary delivery and the auxiliary evacuation, respectively.

As can be understood, the valve 118 is to be actuated at the beginning and/or end of the main delivery of fresh air and of the evacuation of used air, and also at the beginning and/or end of the auxiliary deliveries of fresh air and of the auxiliary evacuations of used air. In this example, the valve 118 is movable between a first position, in which fresh air can be delivered from the gas delivery element 116 to the patient port 114b, and a second position, in which used air can be evacuated from the patient port 114b. FIG. 2A shows the valve 118 in the first position thereby allowing fresh air to be delivered from the gas delivery element 116 to the patient's airway 112 in a first flow direction A, as can be expected to occur in both the main and auxiliary deliveries of fresh air. In contrast, FIG. 2B shows the valve 118 in the second position thereby allowing used air to be evacuated from the patient's airway 112 along a second flow direction B, as can be expected in both the main and auxiliary evacuations of used air. In some embodiments, the valve 118 can include a solenoid valve 122 which is actuatable via one or more control signal(s). In this specific embodiment, the valve 118 is closed when in the first position whereas the valve 118 is closed when in the second position. FIG. 2C shows an example of a valve control signal oscillating between two signal values, in this specific example, to move the valve position between the closed and open positions. As depicted, when the control signal is at a first signal value S1, the valve 118 is in the closed position whereas when the control signal reaches a second signal value S2, the valve 118 is actuated in the open position. The valve control signal may be an electrical signal such as a voltage signal or a current signal. The signal value can correspond to an amplitude of the corresponding electrical signal. In some embodiments, the solenoid valve 122 may have a rest position corresponding to the closed position. Accordingly, the solenoid valve 122 may rest in the closed position, unless a valve control signal carrying a given signal value S is received which will cause the solenoid valve 122 to be moved in the open position. As such, the gas delivery element 116 and the valve 118 may be actuated in a synchronized manner so that the valve 118 be in closed position as fresh air is being delivered by the gas delivery element 116 towards the patient's airway 112 but also so that the valve 118 be in the open position as used air is evacuated through the valve 118 away from the patient's airway 112. Check valve(s) 124 may also be provided to prevent used air from reaching the gas delivery element 116 during the main and auxiliary evacuations of used air, for instance.

Moreover, the gas delivery element 116 is to be actuated at the beginning and/or end of the main delivery of fresh air and of the evacuation of used air, and also at the beginning and/or end of the auxiliary deliveries of fresh air and of the auxiliary evacuations of used air. As shown in FIGS. 3A and 3B, the depicted gas delivery element 116 has a moving element 126 displaceable between a start position Ps corresponding to the start volume Vs and an end position Pe corresponding to the end volume Ve. More specifically, the moving element 126 is displaced at the start position Ps in FIG. 3A, which thereby defines the start volume Vs. In FIG. 3B, the moving element 126 has been moved along an axial direction 128 to the end position Pe which defines the end volume Ve. As shown, the difference between the start and end volumes Vs and Ve corresponds to the main volume Vm that is to be delivered to the patient's airway via the conduit 114 during the main delivery. During the main evacuation, the valve is moved in the open position thereby allowing evacuation of the used air. The check valve(s) 124 can prevent any used air to be drawn towards the gas delivery element 116, especially as the moving element 126 is typically moved back in the start position Ps at least partially during the main evacuation. In some embodiments, the end position Pe of the moving element 126 can act as the start position Ps of a subsequent respiration cycle, and so forth. However, it is preferred to move the moving element 126 in back and forth between the same start and end positions Ps and Ps during subsequent respiration cycles, to reduce the space required for the movement of the moving element 126. In some embodiments, the moving element 126 is provided in the form of a piston 130 which is movable within a cylinder 132. In these embodiments, the start and end positions Ps and Pe correspond to axial positions of the cylinder 132. As shown, the moving element 126 may be moved between these axial positions using a an actuator 134. In some embodiments, the actuator 124 is provided in the form of an electric linear actuator 136.

Figure 4B:
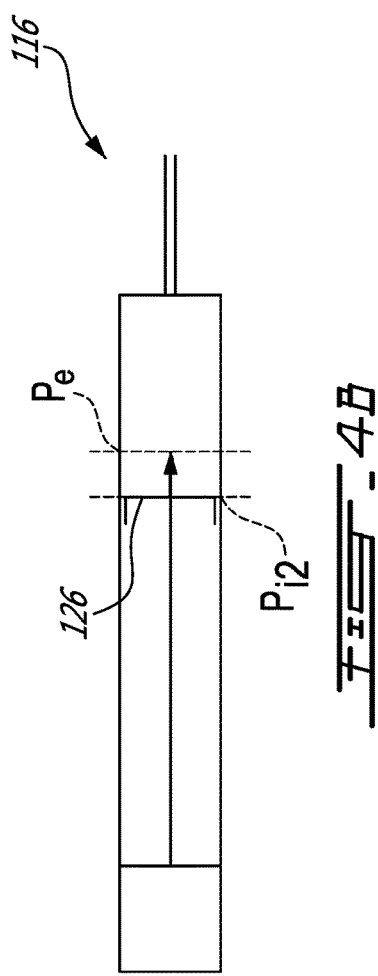
FIG. 4B is a schematic sectional view of the gas delivery element of FIG. 1, shown with the moving element at a second intermediate position, in accordance with one or more embodiments.
Figure 4C:
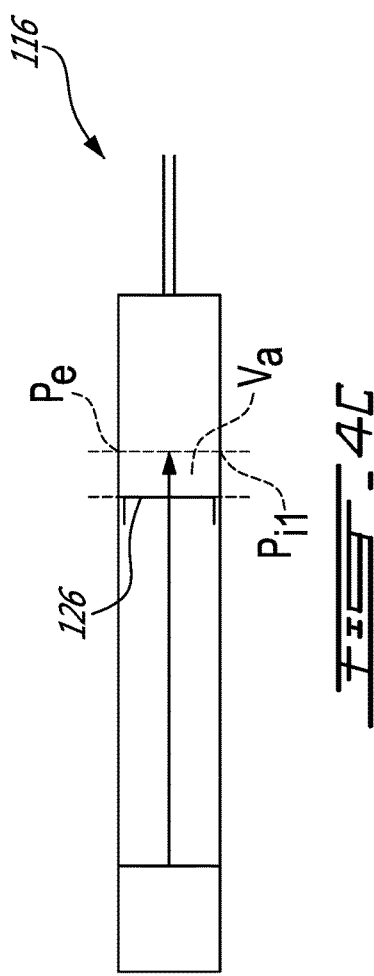
FIG. 4C is a schematic sectional view of the gas delivery element of FIG. 1, shown with the moving element back at the first intermediate position, in accordance with one or more embodiments.

As FIGS. 3A and 3B show the gas delivery element 116 during a main delivery of fresh air, FIGS. 4A through 4C show the gas delivery element 116 during an auxiliary delivery of fresh air and an auxiliary evacuation of used air. More specifically, the moving element 126 is moved from a first intermediate position Pi1, as shown in FIG. 4A, to a second intermediate position Pi2, as shown in FIG. 4B, and then back to the first intermediate position Pi1, as depicted in FIG. 4C. By performing such a back and forth movement between the first and second intermediate positions Pi1 and Pi2, the sequence of alternating auxiliary deliveries of fresh air and evacuations of used air can be performed. In the illustrated embodiment, the alternating auxiliary deliveries of fresh air and evacuations of used air are performed after a main delivery of fresh air. As such, the moving element 126 is moved from the end position Pe to the first intermediate position Pi1, and then back to the second intermediate position Pi2 which in this case coincides with the end position Pe, and so forth. It is noted that the main volume Vm and/or Vm' of air to be delivered and/or evacuated during the main delivery and evacuation is greater than the auxiliary volume Va and/or Va' of air to be delivered and/or evacuated during the auxiliary deliveries and evacuations. Correspondingly, the displacement of the moving element 126 will be greater during the main delivery and evacuation than during the auxiliary deliveries and evacuations. More specifically, the difference between the start and end positions Ps and Pe of the moving element 126 is greater than the difference between the first and second intermediate positions Pi1 and Pi2.

Referring back to FIG. 1, in some embodiments, the ventilator 100 may be provided with a pressure sensor 138 configured to monitor an airway pressure Paw within the conduit 114, the monitored airway pressure Paw being indicative of a pressure within the patient's airway 112. The pressure sensor 138 can be generally provided anywhere within the ventilator 100, provided that it measures the airway pressure Paw as fresh air is delivered to the patient's airway 112 and/or as used air is evacuated from the patient's airway 112. For instance, the pressure sensor 138 may be in fluid communication with within the inlet 114a and/or within the patient port 114b. In some embodiments, a single pressure sensor may be positioned at the inlet 114a or at the patient port 114b, upstream from the valve 118 thereby monitoring the airway pressure Paw regardless of the position of the valve 118. In some other embodiments, more than one pressure sensor can be provided. For instance, a first pressure sensor may be positioned within the inlet 114a to monitor the airway pressure Paw as fresh air is delivered to the patient's airway 112 when the valve position is closed, and a second pressure sensor may be positioned downstream from the valve 118 to monitor the airway pressure Paw when the valve 118 is open. As such, airway pressure Paw may be monitored throughout entire respiration cycles and/or subcycles, during both the main and auxiliary deliveries of fresh air and evacuations of used air.

In some embodiments, the controller 120 may be communicatively coupled to the pressure sensor 138 as well. Such a communicative coupling may be wired, wireless, or a combination of both depending on the embodiment. In some embodiments, the respiration cycles and/or the subcycles may be interrupted or otherwise modified on the go based on airway pressure measurements performed by the pressure sensor 138. In some embodiments, the respiration cycles and/or subcycles may be interrupted or otherwise modified depending on an input received by the controller 120.

In some embodiments, the controller 120 has a processor and a non-transitory memory which has stored thereon instructions that when executed by the processor cause the gas delivery element 116 and the valve 118 to ventilate the patient's airway 112 in accordance with the above-described respiration cycles and subcycles.

More specifically, the controller 120 can be provided as a combination of hardware and software components. The hardware components can be implemented in the form of a computing device 500, an example of which is described with reference to FIG. 5. Moreover, the software components of the controller 120 can be implemented in the form of a software application adapted to perform steps of a method of ventilating a patient's airway, an example of which is described with reference to the flow chart of FIG. 6.

Referring to FIG. 5, the computing device 500 can have a processor 502, a non-transitory memory 504, and I/O interface 506. Instructions 508 for performing method steps (described herein) can be stored on the memory 504 and accessible by the processor 502.

The processor 502 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 504 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. The memory 504 may have stored thereon instructions to actuate the moving element of the gas delivery element between the first, end, first intermediate and second intermediate positions, to actuate the valve between the open and closed positions, and so forth.

Each I/O interface 506 enables the computing device 500 to interconnect with one or more input devices, such as keyboard(s) and mouse(s) and the like, or with one or more output devices such as monitor(s) and remote network(s). For instance, such input devices can be used as a user interface which can be used to input an initial tidal volume which is to be delivered to the patient's airway. The initial tidal volume, which is often referred to as the first tidal volume herein, can be set by an health professional via the user interface. The initial tidal volume associated with the patient may depend on the patient's characteristics (e.g., height, weight, age, gender), the condition of his/her airway and the like. The initial tidal volume may correspond to the main volume Vm. The input devices may also be used to indicate the main respiratory rate Rm at which the respiration cycles, including alternating main deliveries of fresh air and main evacuations of used air, are to be performed. The input devices may also be used to indicate the auxiliary respiratory rate Ra at which the subcycles, including alternating auxiliary deliveries of fresh air and auxiliary evacuations of used air, are to be performed as well. These parameters may be changed on the go, depending on the patient's requirements and evolving clinical conditions.

Each I/O interface 506 enables the controller 120 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., WiMAX), SS7 signaling network, fixed line, local area network, wide area network, and others, including any combination of these.

The computing device 500 described above is meant to be an example only. Other suitable embodiments of the controller 120 can also be provided, as it will be apparent to the skilled reader.

Figure 6:
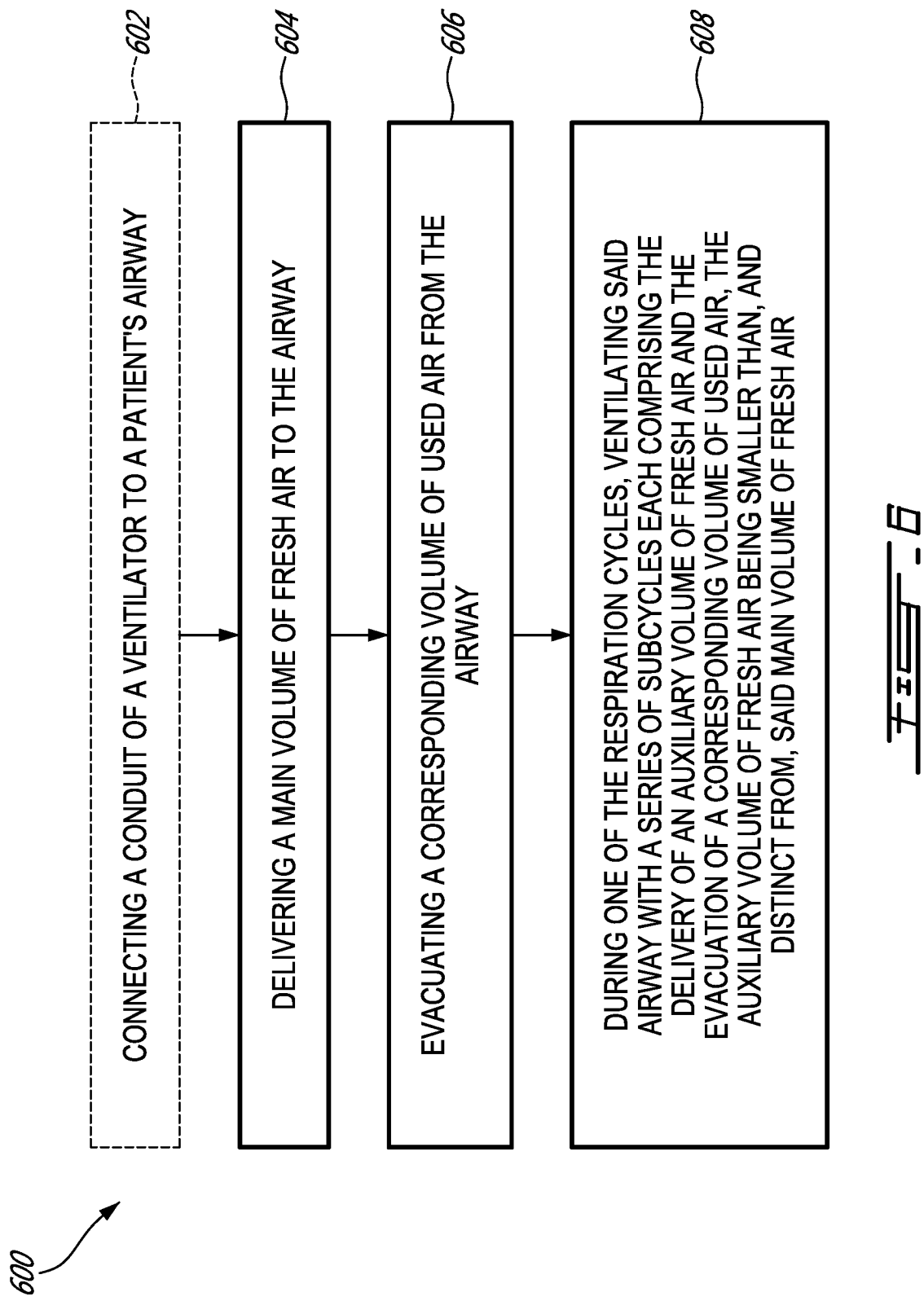
FIG. 6 is a flow chart of a method of ventilating an airway of a patient using the ventilator of FIG. 1, in accordance with one or more embodiments.

Referring now to FIG. 6, there is shown a flow chart of a method 600 for ventilating a patient's airway using the ventilator 100 of FIG. 1. Reference to the ventilator 100 of FIG. 1 will be made in the following paragraphs for ease of reading. It is intended that the controller 120 can have one or more software application(s) configured to perform at least some steps of the method 600.

At step 602, the conduit 114 is connected to the patient's airway 112. This step can be performed by health professional(s) in some embodiments. In some other embodiments, the step 402 can be performed by a suitably programmed robotized machine (not shown).

At step 604, the ventilator 100 is operated to deliver a main volume Vm of fresh air to the patient's airway 112. The delivery of the main volume Vm of fresh air may generate a main pressure variation within the airway 112. For instance, the airway pressure may increase from a base pressure value to a maximal pressure value.

At step 606, the ventilator 100 is operated to evacuate a corresponding volume Vm' of used air from the patient's airway 112. The main evacuation may generate a main pressure variation within the airway 112. In some embodiments, the airway pressure may decrease from the maximal pressure value down to the base pressure value.

At step 608, the ventilator 100 is operated to ventilate the airway 112 with subcycles comprising alternating auxiliary deliveries of auxiliary volumes Va of fresh air and auxiliary evacuations of corresponding volume Va' of used air. The auxiliary deliveries and auxiliary evacuations may generate auxiliary pressure variations within the airway 112. The auxiliary volumes Va and Va' may differ from one subcycle to another, in some embodiments. However, as noted above, the auxiliary volumes Va and Va' are smaller than, and distinct from, the main volume Vm of the corresponding respiration cycle. In some embodiments, the auxiliary volume is 50% smaller than the main volume, preferably 30% smaller than the main volume and most preferably 20% smaller than the main volume.

In some embodiments, the auxiliary pressure variations are of significantly lower amplitude than the main pressure variations. For instance, the auxiliary pressure variations can be 50% smaller than the main pressure variations, preferably 30% smaller than the main pressure variations and most preferably 20% smaller than the pressure variations. The auxiliary pressure variations may vary over time according to a sinusoidal-like shape. The amplitude and/or frequency of those sinusoidal-like pressure variations may change from one embodiment to another.

It is noted that for patients infected with some respiratory diseases, for instance COVID-19, their lungs may have lung tissues which are stiffer than regular, healthy lung tissues, and therefore more difficult to satisfactorily recruit. In these situations, the delivery of the main volume of fresh air can recruit at least the softer lung tissues of the infected lungs while the subcycles can recruit the stiffer lung tissues of the infected lungs. Simulations demonstrating that stiffer lung tissues recruitment is advantageously increased by performing the subcycles described herein have been made.

In some embodiments, the method 600 has an optional step of monitoring an airway pressure Paw of the patient during the operation of the ventilator. In these embodiments, the respiration cycles and/or subcycles may be modified on the go based on said monitored airway pressure Paw.

In some embodiments, the method 600 has an optional step of interrupting the subcycles, and/or the respiration cycles, contingent upon receiving a corresponding input. For instance, in some embodiments, such input may be received via a user interface of the controller. The respiration cycles and/or the subcycles may also be interrupted based on an airway pressure threshold being produced. The subcycles may be designed so that a maximal tidal volume is not reached during the subcycles.

In some embodiments, alarms are outputted by the controller upon determining that subcycles of auxiliary deliveries of fresh air and auxiliary evacuations of used used should preferably be performed and/or interrupted. In some embodiments, the ventilation of the patient's airway is performed in a manner which prevent spontaneous breaths of the patient. Preferably, in some embodiments, the subcycles are performed during periods of time where any spontaneous breaths of the patient are not allowed.

Figure 7:
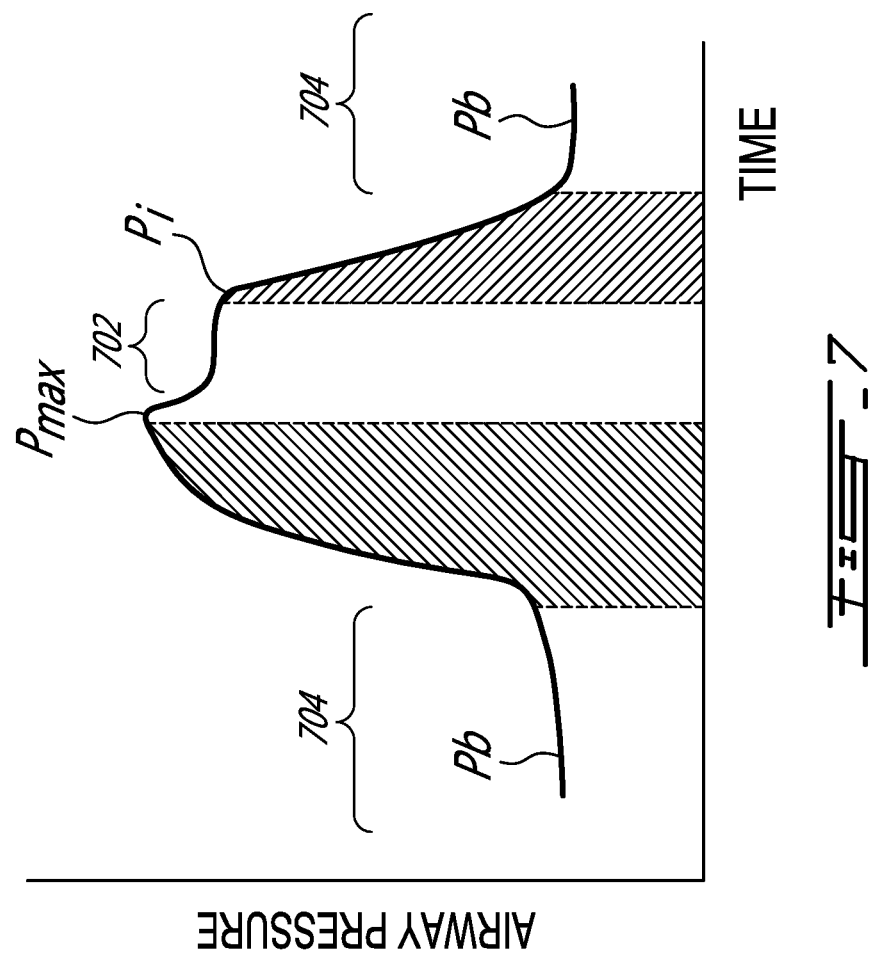
FIG. 7 is a graph showing airway pressure as a function of a respiration cycle, showing an inspiration phase, a pause, followed by an expiration phase and another pause.

FIG. 7 shows the pressure variations caused by the main delivery of fresh air of step 604 and by the main evacuation of used air of step 606. As shown, as fresh air is delivered, the airway pressure Paw increases from a base pressure value Pb to a maximal pressure value Pmax, after which a pause 702 is observed. In this example, the airway pressure Paw decreases from the maximal pressure value Pmax down to an intermediate pressure value Pi. The pause 702 is observed at the intermediate pressure value Pi in this specific embodiment. As used air is evacuated from the patient's airway, the airway pressure Paw decreases from the maximal pressure value Pmax and/or any intermediate pressure value Pi back to the base pressure value Pb. As such, the ventilation cycle comprises an inspiration phase comprising the main delivery of fresh air, where airway pressure increases gradually, and the pause 702, and an expiration phase comprising the main evacuated of used air, where airway pressure decreases gradually, and another pause 704. The alternating auxiliary deliveries of fresh air and evacuations of used air may be performed during at least one or both of the inspiration phase and the expiration phase. More specifically, the alternating auxiliary deliveries of fresh air and evacuations of used air may be performed during the either one of the pauses 702 and 704, examples of which are described with reference to FIGS. 8A through 10B.

FIG. 8A shows airway pressure Paw during an example respiration cycle having in succession an inspiration phase 802 having a main delivery 802a and a pause 802b, and an expiration phase 804 having a main evacuation 804a and another pause 804b. In this embodiment, the airway pressure Paw increases from base pressure value Pb to a maximal pressure value Pmax during the main delivery 802a. The airway pressure Paw stays at the maximal pressure value Pmax for the duration of the pause 802b. Then, the airway pressure Paw decreases from the maximal pressure value Pmax to the base pressure value Pb during the main evacuation 804a, and stays there for the duration of the pause 804b. Superposed to this example respiration cycle are a plurality of subcycles comprising auxiliary deliveries 806 of fresh air and auxiliary evacuations 808 of used air. More specifically, in this example, the subcycles are distributed during the pause 802b. In some embodiments, the subcycles may start a given period of time after the main delivery 802a. In this example, the series of subcycles are performed as the lungs of the patient are recruited by the main volume of fresh air. FIG. 8B shows a graph of an exemplary valve control signal during the ventilation cycle of FIG. 8A. As shown, the valve is moved between the open and closed positions whenever a main or auxiliary delivery of fresh air, or a main or auxiliary evacuation of used air, occurs.

FIG. 9A shows airway pressure during an example respiration cycle having in succession an inspiration phase 902 having a main delivery 902a and a pause 902b, and an expiration phase 904 having a main delivery 904a and another pause 904b, such as those described above. Superposed to this example respiration cycle are a plurality of subcycles comprising auxiliary deliveries 906 of fresh air and auxiliary evacuations 908 of used air. More specifically, in this example, the subcycles are distributed during the pause 904b of the expiration phase 904, immediately after the main evacuation 904a of used air. In some other embodiments, the subcycles may start a given period of time after the main evacuation 904a. In this example, the series of subcycles are performed as the lungs of the patient are empty or almost empty. FIG. 9B shows a graph of an exemplary valve control signal during the ventilation cycle of FIG. 9A. As shown, the valve is moved between the open and closed positions whenever a main or auxiliary evacuation of used air occurs, otherwise the valve remains closed so that fresh air be deliverable into the lungs of the patient.

FIG. 10A shows airway pressure during an example respiration cycle having in succession an inspiration phase 1002 having a main delivery 1002a and a pause 1002b, and an expiration phase 1004 having a main delivery 1004a and another pause 1004b such as those described above. In this specific embodiment, a first series of subcycles comprising auxiliary deliveries 906 of fresh air and auxiliary evacuations 908 of used air are performed during the pause 1002b of the inspiration phase 1002. In addition, a second series of subcycles comprising auxiliary deliveries 906 of fresh air and auxiliary evacuations 908 of used air are performed during the pause 1004b of the expiration phase 1004. FIG. 10B shows a graph of an exemplary valve control signal during the ventilation cycle of FIG. 10A.

FIG. 11 shows another example of a ventilator 1100 to ventilate an airway 1112 of a patient, in accordance with one or more embodiments. As depicted, the ventilator 1100 has a conduit 1114 which is in this case provided in the form of a Y-piece having a an inlet 1114a, a patient port and an evacuation port 1114c. As shown, the inlet 1114a is in fluid communication to the patient port 1114b and thus to the patient's airway 1112.

The ventilator 1100 has a gas delivery element 1116 which is in fluid communication with the inlet 1114a of the conduit 1114. As shown, the gas delivery element 1116 is configured to deliver air in a sequence of ventilation cycles and subcycles as described above. The gas delivery element 1116 has a cylinder 1132 within which a piston 1126 moves. By moving the piston 1126 from a start position Ps to an end position Pe, corresponding main or auxiliary volumes Vm and Va can be delivered to the patient's airway 1112. In this specific example, the gas delivery element 1116 has an actuator 114, e.g., an electrical linear actuator 1136, which is mechanically coupled to the piston 1126, and sealed relative to the cylinder 1132. The actuator 1134 can move the piston 1126 in a sequence of back and forth at different axial positions based on one or more electrical signals.

As shown, the ventilator 1100 draws fresh air from the surrounding environment 1152, which may be filtered using a fresh air filter 1154. As shown, an oxygen source 1156 may be used to increase the oxygen content of the surrounding fresh air that is drawn by the ventilator 1100. As such, when the piston 1126 from the gas delivery element 1116 is pulled backward, fresh air from the surrounding environment 1152, and also oxygenated by the oxygen source 1156, may be drawn within the ventilator 1100, and more specifically within a given portion of the cylinder 1132, ready to be delivered into the patient's airway 1112 by pushing the piston 1126 in an opposite direction towards the conduit 1114. A first check valve 1158 upstream from the gas delivery unit 1116 may be used to control entry of fresh air within the ventilator 1100. A second check valve 1160 downstream from the gas delivery unit 1126 may be used to prevent air from reaching the gas delivery unit 1116 once it has been breathed or otherwise used by the patient's airway 1112. A solenoid valve 1162 may be provided downstream from the conduit 1114, and more specifically downstream from the evacuation port 1114c of the Y-piece conduit. The solenoid valve 1162 may be operated to be either closed, thereby favoring a fresh air flow between the gas delivery unit 1116 and the patient's airway 1112, or open, thereby favoring a used air flow between the patient's airway 112 and a remainder of the ventilator 1100 or ultimately the surrounding environment 1152, where used air is to be evacuated. A PEEP valve 1164 may also be provided downstream from the evacuation port 1114c and upstream from the solenoid valve 1162. The PEEP valve 1164 may be a spring loaded valve that the patient's airway 1112 may exhale against when needed. As such, the PEEP valve 1164 may prevent ventilator induced lung injury. Additional air filter may be provided upstream from the inlet 1114a and downstream from the evacuation port 1114c, as shown in this specific embodiment. An enlarged view of the solenoid valve 1162 and of the PEEP valve 1164 is shown in FIG. 12.

Referring back to FIG. 11, the ventilator 1100 has a pressure sensor 1138 configured to monitor pressure Paw within the conduit 1114. In this example, the pressure sensor 1138 is a single pressure sensor which is located upstream from the inlet 1114a. The pressure sensor 1138 has a gauge 1150 displaying the instantaneous pressure value within the conduit 1114. The pressure sensor 1138 generates signal(s) and/or data indicative of the instantaneous pressure value.

A controller 1120, in this example provided in the form of a computer, is also provided. As shown, the controller 1120 and the pressure sensor 1138 are communicatively coupled to one another via wired connections. The signal(s) and/or data generated by the pressure sensor 1138 in real time are communicated to the controller 1120 which may locally or remotely process, compare and/or store them as they are received. The controller 1120 is also communicatively coupled to the gas delivery unit 1116 via a wired connection to control the actuator, for instance. The controller 1120 may also be communicatively coupled to the solenoid valve 1162 via a wired connection to control it as desired.

Figures 13A, 13B, 13C:
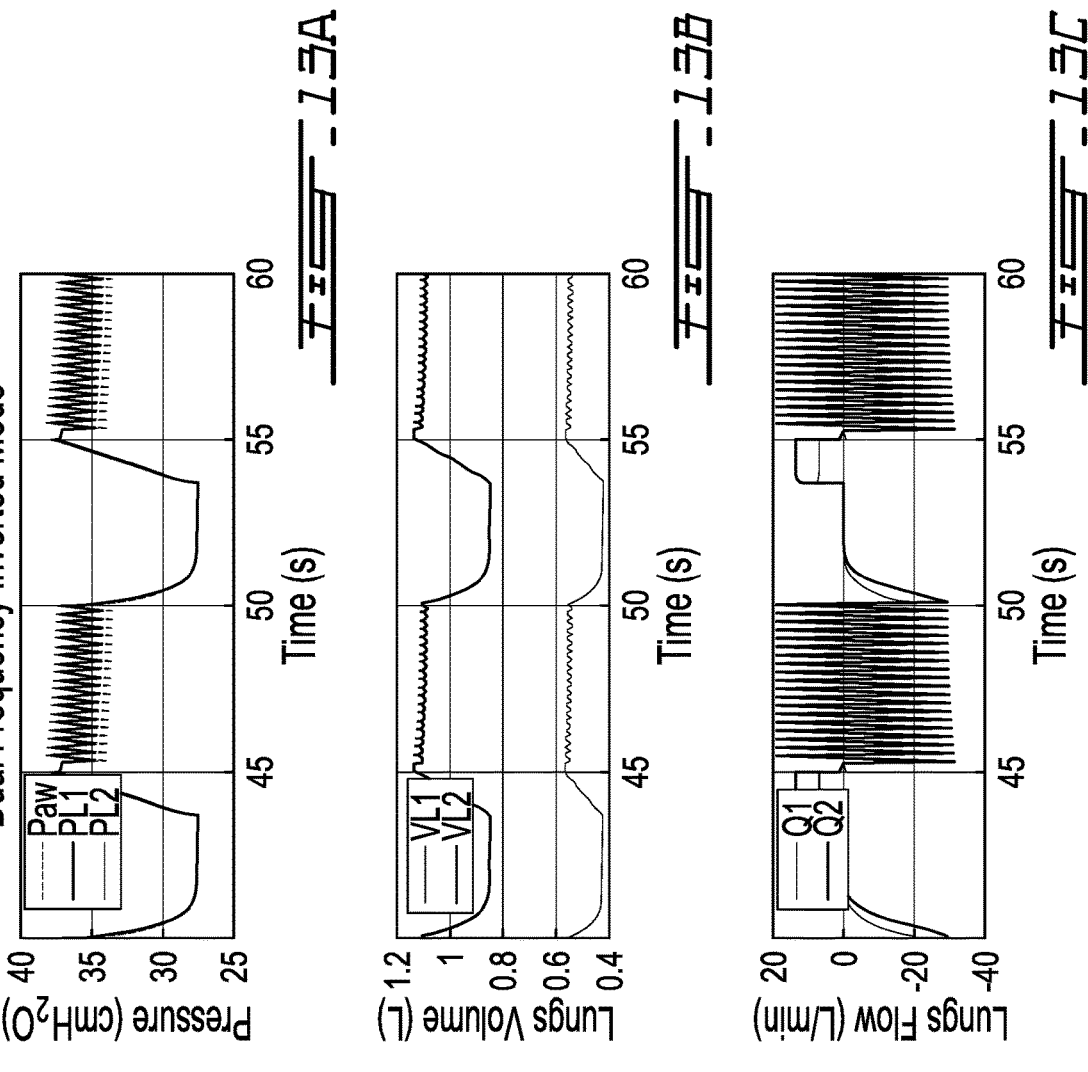
FIG. 13A is a graph showing airway pressure as a function of time during exemplary respiration cycles performed by the ventilator of FIG. 11, in accordance with one or more embodiments.
FIG. 13B is a graph showing lung volume as a function of time during the exemplary respiration cycles of FIG. 13A, in accordance with one or more embodiments.
FIG. 13C is a graph showing lung flow as a function of time during the exemplary respiration cycles of FIG. 13A, in accordance with one or more embodiments.

FIGS. 13A, 13B and 13C show the airway pressure, the lung volume, and the lung flow as a function of time during a number of ventilation cycles comprising main deliveries of fresh air and main evacuation of used air as well as a series of alternating auxiliary deliveries of fresh air and auxiliary evacuations of used air.

It will be understood that the expression "controller" as used herein is not to be interpreted in a limiting manner. It is rather used in a broad sense to generally refer to the combination of some form of one or more processing units and some form of memory system accessible by the processing unit(s). The memory system can be of the non-transitory type. The use of the expression "controller" in its singular form as used herein includes within its scope the combination of a two or more computers working collaboratively to perform a given function. Moreover, the expression "controller" as used herein includes within its scope the use of partial capabilities of a given processing unit.

It will be understood that a controller can perform functions or processes via hardware or a combination of both hardware and software. For example, hardware can include logic gates included as part of a silicon chip of a processor. Software (e.g. application, process) can be in the form of data such as computer-readable instructions stored in a non-transitory computer-readable memory accessible by one or more processing units. With respect to a controller or a processing unit, the expression "configured to" relates to the presence of hardware or a combination of hardware and software which is operable to perform the associated functions.

The embodiments described in this document provide non-limiting examples of possible implementations of the present technology. Upon review of the present disclosure, a person of ordinary skill in the art will recognize that changes may be made to the embodiments described herein without departing from the scope of the present technology. For instance, the respiration cycles and subcycles may be performed using a mechanical system moving the moving element of the gas delivery element and actuating the valve based on a computer-less system. Yet further modifications could be implemented by a person of ordinary skill in the art in view of the present disclosure, which modifications would be within the scope of the present technology.

The invention claimed is:

1. A ventilator to ventilate an airway of a patient, the ventilator comprising:
   a conduit having an inlet in fluid communication with a patient port, said patient port being configured to be fluidly connected to said airway;
   a gas delivery element fluidly connected to said inlet and configured for selectively delivering fresh respiratory gas into the conduit;
   a valve fluidly connected to said conduit, said valve being selectively operable to vent the conduit and thereby evacuate used respiratory gas via the patient port; and
   a controller configured to alternatingly control the gas delivery element and the valve in a series of respiration cycles, wherein each respiration cycle includes a delivery of a main volume of fresh respiratory gas into the conduit, followed by an evacuation of a corresponding main volume of used respiratory gas,
   said controller being further configured to alternatingly control the gas delivery element and the valve in a series of subcycles during a corresponding one of the respiration cycles, wherein each subcycle includes a delivery of an auxiliary volume of fresh respiratory gas into the conduit, followed by an evacuation of a corresponding auxillary volume of used respiratory gas, the auxiliary volume being smaller than, and distinct from, the main volume.

2. The ventilator of claim 1 wherein said auxiliary volume is 50% smaller than said main volume.

3. The ventilator of claim 1 wherein said series of subcycles are performed during at least a portion of at least one of an inspiration phase and an expiration phase of said respiration cycles.

4. The ventilator of claim 1 wherein said valve is actuatable between a first position, in which the fresh respiratory gas is delivered to the patient port, and a second position, in which the used respiratory gas is evacuated from said patient port.

5. The ventilator of claim 1 wherein said delivery of said main volume of fresh respiratory gas causes a main pressure variation within the airway, said delivery of said auxiliary volume of fresh respiratory gas causing an auxiliary pressure variation within the airway, the auxiliary pressure variation being of significantly lower amplitude than said main pressure variation.

6. The ventilator of claim 5 wherein said auxiliary pressure variation is 50% smaller than said main pressure variation.

7. The ventilator of claim 1 further comprising a pressure sensor configured to monitor pressure within said conduit, said delivery of said main and auxiliary volumes of fresh respiratory gas being dependent on said monitored pressure.

8. A method of ventilating an airway of a patient, said method comprising:
   ventilating said airway of said patient in accordance with a series of respiration cycles, each respiration cycle including a delivery of a main volume of fresh respiratory gas into said airway, followed by an evacuation of a corresponding main volume of used respiratory gas; and
   during a corresponding one of said respiration cycles, ventilating said airway of said patient in accordance with a series of subcycles, wherein each subcycle includes a delivery of an auxiliary volume of fresh respiratory gas into the airway, followed by an evacuation of a corresponding auxillary volume of used respiratory gas, the auxiliary volume being smaller than, and distinct from, the main volume.

9. The method of claim 8 wherein said auxiliary volume is 50% smaller than said main volume.

10. The method of claim 8 wherein said series of subcycles are performed during at least a portion of at least one of an inspiration phase and an expiration phase of said respiration cycles.

11. The method of claim 8 wherein said respiration cycles include at least a pause between said delivery of said main volume of fresh respiratory gas and said evacuation of said corresponding main volume of used respiratory gas, said series of subcycles being performed during said pause.

12. The method of claim 11 wherein said pause is immediately following said delivery of said main volume of fresh respiratory gas, said series of subcycles being performed as lungs of said patient are recruited by said main volume.

13. The method of claim 8 wherein said alternating deliveries of fresh respiratory gas and evacuations of used gas recruit stiffer lung tissues of said patient.

14. The method of claim 8 wherein said delivery of said main volume of fresh respiratory gas causes a main pressure variation within the airway, said delivery of said auxiliary volume of fresh respiratory gas causing an auxiliary pressure variation within the airway, the auxiliary pressure variation being of significantly lower amplitude than said main pressure variation.

15. The method of claim 14 wherein said auxiliary pressure variation is 50% smaller than said main pressure variation.

16. The method of claim 14 wherein said auxiliary pressure variation varies sinusoidally over time.

17. The method of claim 8 further comprising monitoring an airway pressure of said patient, said respiration cycles and said subcycles being dependent on said monitored airway pressure.

18. The method of claim 8 wherein said series of subcycles are performed at a rate at least ten times greater than a main respiratory rate of said respiratory cycles.

19. The method of claim 8 further comprising interrupting said subcycles contingent upon receiving an input.

20. A computer program product stored in a non-transitory memory of a controller further having a processor, the computer program product having computer readable instructions which, when executed by the processor controls a patient ventilator, including the steps of: ventilating a conduit of said patient ventilator in accordance with a series of respiration cycles, each respiration cycle including a delivery of a main volume of fresh respiratory gas into said conduit, followed by an evacuation of a corresponding main volume of used respiratory gas; and during a corresponding one of said respiration cycles, ventilating said respiration cycle including the delivery of the main volume of fresh respiratory gas into said conduit of said patient in accordance with a series of subcycles, wherein each subcycle includes a delivery of an auxiliary volume of fresh respiratory gas into the respiration cycle including the delivery of the main volume of fresh respiratory gas into said conduit, followed by an evacuation of a corresponding auxillary volume of used respiratory gas, the auxiliary volume of fresh respiratory gas being smaller than, and distinct from, the main volume of respiratory gas.

* * * * *